(12) United States Patent
Vihko

(10) Patent No.: US 7,919,671 B2
(45) Date of Patent: Apr. 5, 2011

(54) METHOD FOR TESTING A COMPOUND FOR A THERAPEUTIC EFFECT AND A DIAGNOSTIC METHOD

(75) Inventor: Pirkko Vihko, Helsinki (FI)

(73) Assignee: Chempath Oy, Helsinki (FI)

( * ) Notice: Subject to any disclaimer, the term of this patent is extended or adjusted under 35 U.S.C. 154(b) by 797 days.

(21) Appl. No.: 11/667,238

(22) PCT Filed: Nov. 11, 2005

(86) PCT No.: PCT/FI2005/050417
§ 371 (c)(1),
(2), (4) Date: Jun. 4, 2007

(87) PCT Pub. No.: WO2006/051172
PCT Pub. Date: May 18, 2006

(65) Prior Publication Data
US 2007/0292350 A1 Dec. 20, 2007

(30) Foreign Application Priority Data
Nov. 11, 2004 (FI) ........................................ 20041453

(51) Int. Cl.
*G10N 33/00* (2006.01)
*A01K 67/00* (2006.01)
*A01K 67/027* (2006.01)
(52) U.S. Cl. .................................. 800/3; 800/8; 800/18
(58) Field of Classification Search .................. 800/3, 8, 800/18
See application file for complete search history.

(56) References Cited

FOREIGN PATENT DOCUMENTS

| WO | 0043548 A1 | 7/2000 |
| WO | 02063013 A2 | 8/2002 |
| WO | 2004096153 A2 | 11/2004 |

OTHER PUBLICATIONS

Kaneko et al., 1995, Internal Med., vol. 34 pp. 886-891.*
2004, Barthold S., Genetica, vol. 122, pp. 75-88.*
2009, Doetschman T., Methods Mol. Biol., vol. 530, pp. 423-433.*
2004, Crusio et al., Biol. Psychiatry, vol. 56, pp. 381-385.*
Moreadith, 1997, J. Mol. Med., vol. 75 pp. 208-216.*
Prelle, 1999, Cell Tissues Organs, vol. 165, pp. 220-236.*
Smith, Journal of Biotechnology, vol. 99, pp. 1-22, 2002.*
Denning et al. Reproduction, vol. 126, pp. 1-11, 2003.*
Baker et al., 2000, Int. J. Human-Computer Studies, vol. 52 pp. 1-16.*
"Suppression of LNCaP prostate cancer xenograft tumors by a prostate-specific protein tyrosine phosphatase, prostatic acid phosphatase", T. Igawa et al., The Prostate, Apr. 18, 2003, vol. 55, pp. 247-258.
"Prostate-specific deletion of the murine Pten tumor suppressor gene leads to metastatic cancer," S. Wang et al., Cancer Cell, Sep. 2003, vol. 4, pp. 209-221.
"Prostatic acid phosphatase (PAP) is (P1(3)P-phosphatase and its inactivation leads to change of cell polarity and invasive prostate cancer," P. T. Vihko et al., Apr. 19, 2005; Proceedings of the AACR, $9^{th}$ annual meeting, Apr. 16-20, 2005.
"Decreased Expression of Cellular Prostatic Acid Phosphatase Increases Tumorigenicity of Human Prostate Cancer Cells," Lin et al., The Journal of Urology, Nov. 2001, vol. 166, pp. 1943-1950.
"Genetically defined mouse models that mimic natural aspects of human prostate cancer development," Roy-Burman et al., Endocrine-Related Cancer, Jun. 2004, vol. 11, No. 2, pp. 225-254.
Hakalahti et al., "Evaluation of PAP and PSA Gene Expression in Prostatic Hyperplasia and Prostatic Carcinoma Using Northern-Blot Analyses, in Situ Hybridization and Immunohistochemical Stainings with Monoclonal and Bispecific Antibodies", International Journal of Cancer, vol. 55, No. 4, 1993, pp. 590-597, XP002519632.
Chu et al., "PSA and Acid Phosphate in the Diagnosis of Prostate Cancer", Journal of Clinical Ligand Assay, vol. 21, No. 1, Apr. 1998, pp. 24-34, XP009113612.
European Search Report dated Mar. 19, 2009 from corresponding EP Application No. 05813227.5.

* cited by examiner

*Primary Examiner* — Peter Paras, Jr.
*Assistant Examiner* — David Montanari
(74) *Attorney, Agent, or Firm* — Young & Thompson

(57) ABSTRACT

A method for testing compound for a therapeutic effect utilizing a non-human animal or cell having disruption in the prostatic acid phosphatase gene resulting in a decrease or absence in the activity or the level of prostatic acid phosphatase. The compound may be used for treating disorders related to unbalanced phosphatidylinositol phosphate cascade or signaling pathway. Diagnostic methods and methods for treating the disorders with therapeutic compounds or by gene therapy are also disclosed.

6 Claims, 8 Drawing Sheets

METHOD FOR TESTING A COMPOUND FOR A THERAPEUTIC EFFECT AND A DIAGNOSTIC METHOD

FIELD OF THE INVENTION

The present invention relates to methods for testing and screening for a compound for a therapeutic effect for treating disorders related to unbalanced phosphatidy-linositol phosphate cascade and/or signaling pathway. More particularly the present invention relates to methods utilizing a prostatic acid phosphatase knockout non-human animal model. The present invention also relates to diagnostic methods and methods for treating disorders related to phosphatidylinositol phosphate cascade and signaling pathway.

BACKGROUND OF THE INVENTION

Mammalian prostatic and lysosomal acid phosphatases (EC 3.1.3.2.) include a covalent phosphohistidine intermediate in their reaction mechanism, and they are thus called histidine acid phosphatases. The same histidine acid phosphatase group includes *E. coli* pH 2.5 acid phosphatase and glucose-1-phosphatase, yeast acid phosphatases, *Aspergillus* phytases A and B, and *E. coli* phytase. *E. coli* phytase catalyzes the sequential hydrolysis of phosphate phytate (myo-inositol-1,2,3,4,5,6-hexakisphosphate, $IP_6$) to less phosphorylated myo-inositol derivatives and inorganic phosphate. $IP_6$ and its derivatives have functions in RNA export, DNA repair, and DNA recombination and in endocytosis and vesicular trafficking.

The inventor's earlier structural studies of PAP showed that the α/β domain resembles the structure of phosphoglycerate mutase. This domain contains a sequence motif that is also present in the bifunctional phosphofructokinase/fructose bisphosphatase. The active site of PAP is a rather open, readily accessible cleft. Despite low sequence homology (14% identity), the crystal structure of *E. coli* phytase is closely related to PAP. The histidine residue in the conserved motif, RHGXRXP, serves as a nucleophile in the formation of a covalent phosphohistidine intermediate, and the aspartic acid residue of the C-terminal conserved histidine domain motif serves as a proton donor to the oxygen atom of the phosphoester bond.

There are two forms of PAP, intracellular and secreted. The physiological substrate of hPAP has been unclear. It has been suggested that the growth-suppressing effect of hPAP is due to its intrinsic protein tyrosine phosphatase activity, and this suggestion was supported by theoretical modelling and molecular-dynamic simulation methods, which demonstrated that EGFR and its homologue ErbB-2 could be possible in vivo ligands. The theory is further supported by the declining phosphorylation status of ErbB-2 after intratumoral administration of hPAP cDNA. However, hPAP has also been shown to be a universal protein phosphatase that hydrolyzes equally well the phosphotyrosine, -serine, and -threonine residues.

Within cells, the activity of hPAP is lower in prostate carcinomas than in normal prostates, and both hPAP mRNA and protein levels are decreased or absent in prostate carcinoma tissue. Similar effects can be observed in prostate cancer cell lines: the hPAP-expressing LNCaP cell line has a slower proliferation rate than the non-expressing PC-3 and DU-145 cells. Studies with transfected hPAP support the growth-suppressing effect. The present inventor has earlier demonstrated the binding of hPAP to the main high-density lipoprotein apolipoprotein A-1 (apoA-1). ApoA-1 is lipidated during its progress through intracellular vesicle traffic from the cell surface lipid raft into early endosomes, late endosomes, and finally back to the cell surface as a nascent HDL particle.

Animal models, such as transgenic or knockout animal models, may be used to investigate disorders related to certain genes. One such disorder is prostate cancer or tumor, which has been shown in the current invention to be associated with prostatic acid phosphatase in a specific way. In the art there are some known animal models which promote the formation of prostate tumor. For example review publication "Genetically defined mouse models that mimic natural aspects of human prostate cancer development" (Roy-Burman et al., Endocrine-Related Cancer (2004) 11:225-254) discloses several known mouse models for prostate cancer and exploitation thereof. This and all the other publications and other material disclosed herein are incorporated by reference.

The PTEN (phosphatase and tensin homolog deleted on chromosome 10) tumor suppressor gene is one of the most frequently mutated/deleted genes in various human cancers. For example Wang et al. (Cancer Cell 4, 209-221) disclose a murine PTEN prostate cancer model.

WO 2004096153 describes prostate cancer therapeutics and speculates on animal models having knockout prostatic acid phosphatase gene. However, no actual animal models were disclosed.

SUMMARY OF THE INVENTION

The present invention is based on the finding that decrease or absence of the activity of prostatic acid phosphatase (PAP) is related to certain disorders not associated to PAP before. These diseases and disorders relate to unbalanced phosphatidylinositol 3-phosphate (PI(3)P) and $PI(4,5)P_2$ signaling pathway.

One aspect of the present invention relates to a method for testing and screening for compound for an therapeutic effect, said method comprising the steps of administering said compound to a cell or a non-human animal having disruption in the prostatic acid phosphatase gene or regulation thereof resulting in a decrease or absence of the activity or the level of prostatic acid phosphatase, and determining if said compound substantially restores the unbalanced phosphatidylinositol phosphate signaling pathway related to PAP expression or activity on said cell or said animal, said restoring indicating said compound being therapeutically effective for treating disorders related to unbalanced phosphatidylinositol phosphate signaling pathway. The response of said restoring may be decrease in $PI(4,5)P_2$ accumulation or decrease in the level of PI(3)P, caused by the recovered PAP activity or level of expression. The term "substantially restoring" as used herein refers to such restoration or normalization of unbalanced PIP signaling pathway, either complete or partial, which has therapeutic value and effect. These methods may be used for investigating diseases and disorders related to PAP, such as prostate hypertrophy, tumors or cancer. Such methods include for example testing and screening of drug candidate compound or the like.

Another aspect of the present invention relates to diagnostic method wherein the increased level of $PI(4,5)P_2$ is used to indicate the presence of a disease or disorder related to unbalanced phosphatidylinositol phosphate signaling pathway.

One aspect of the present invention relates to therapeutic compounds obtained by said screening method.

Another aspect of the current invention relates to methods for treating disorders related to unbalanced phosphatidylinositol phosphate cascade and/or signaling pathway related to prostatic acid phosphatase resulting in $PI(4,5)P_2$ accumulation, increased level of PI(3)P or increased ratio of PI(4,5)P$_2$/PI(4)P, by administering a patient suffering said disorder compound which increases the level of expression or activity of PAP or by giving said patient gene therapy which increases the level or restores the activity of PAP.

The present invention utilizes a knockout animal model wherein the prostatic acid phosphatase gene in the genome of said animal has been disrupted resulting in a decrease in the activity or the level of prostatic acid phosphatase. Said knockout animal expresses a reduced level or activity of PAP enzyme in certain cells or tissues or preferably does not express PAP at all.

Also an isolated knockout animal or plant cell, such as a prostate cell, may be used. Such cells may be cultured and used to investigate disorders related to PAP and its function. The animals described above may be used as a source of said cells. In one embodiment said cell may be a human cell line, such as one derived from a human cancer cell line.

The inventor of the present invention has shown that PAP, which is a tyrosine phosphatase, is also a lipid phosphatase and it effectively dephosphorylates phosphatidylinositol 3-phosphate. The removal of PAP activity for example inflicts changes in the prostate in every animal in the anterior (AP) and dorsolateral (DLP) lobes. These animals are viable and fertile and they develop benign prostate hyperplasia followed by initiation of prostate cancer with prostate intraepithelial neoplasia (PIN) and invasive adenocarcinoma. In DLP PAP co-localizes with PI(3)P subcellularly on the endosomal pathway. The results also show that PAP is not only an important regulator of PI(3)P transport, but also a novel tumor suppressor of prostate epithelial cells.

PAP dephosphorylates phosphatidylinositol 3-phosphate, which is a phospholipid. Inactivation of PAP leads to inbalance of phosphoinositide (phosphatidylinositol phosphate) cascade and to increase of PI(3)P and even more remarkable increase of PI(4,5)P$_2$. This leads to changes in membrane and vesicular traffic and cytoskeleton of the cell. In addition G-protein and small GTPase signaling is changed. In addition PAP is connected to cholesterol transport and it has cholesterol binding domains. Unbalanced PI-cascade is also dependent on cell lipid metabolism. Diseases like prostate, bladder and pancreatic cancer, myopathy (myodegeneration) and neuropathy (neurodegeneration) may be caused by said inbalanced PI-cascade.

The knockout animal or cell model may be utilized in several ways. It may be used when investigating prostatic intraephitelial neoplasia or other disorders related to prostatic acid phosphatase and function thereof. It may also be used when developing and screening drugs for treating such diseases. Also the roles of certain hormones related to said disorders may be investigated. The animal or cell model of the present invention is directed not only to prostate cells but any other cell or tissue types naturally expressing PAP. The same disease mechanism may lead to cancer or other disorders of said other cells or tissues, such as salivary gland, kidney, lung, granulocytes, Langerhans cells, muscle, Schwann cells or other cells and tissues.

The knocking out of naturally existing enzyme, such as PAP, will provide a useful model for investigating disorders related to said enzyme. The model used in the present invention utilizes a simple approach of switching off a naturally existing PAP enzyme activity (e.g. in the prostate) as such decrease in said activity is now known to be related to certain disorders, such as prostatic intraepithelial neoplasia (PIN) and carcinoma.

(A) Partial structure of the PAP gene and the targeting construct are shown. The coding exons are indicated as filled boxes. An arrow shows the transcriptional orientation in neo gene. Tk gene was added at the end of the targeting construct as a negative screening tool. Locations of the oligonucleotides used in the PCR screening are marked with an asterisk (5'-TGCTGCACGGATACACATGC-3') (SEQ ID NO: 1) and a point (5'-TCGCAGCGCATCGCCTTCT-3') (SEQ ID NO: 2).

(B) AvrII digested genomic DNA isolated from PAP$^{+/+}$, PAP$^{+/-}$ and PAP$^{-/-}$ mice was separated by electrophoresis and transferred onto nylon membrane. The blot was hybridized by $^{32}$P-labeled probe (location marked by a line above the gene structure in FIG. 1A. The 18.3 kb fragment represents the wild type allele between the AvrII sites in the first and seventh introns. Size of the targeted allele with neo gene is 19.5 kb.

(C) Modeled binding of PI(3)P in the active site of PAP. Possible hydrogen bonds to PI(3)P are shown as stippled gray lines, but for clarity those involving the 3-phosphate group are not included and only polar interactions are shown. Only PI with a P in position 3 is able to align for hydrolysis and at the same time give good interactions to the inositol ring and the 1-phosphate group. Introduction of further phosphate groups to the inositol ring brings about no favorable interactions, and in some instances it causes steric hindrance. The hydrogen bond interactions with Tyr123, Arg127 and Ser175 are specific to prostatic acid phosphatase; these residues are not conserved in lysosomal acid phosphatase.

(D) The phospholipid binding properties of PAP. Nitrocellulose-immobilized phospholipids at 100 pmole per spot. The lipids, indicated by dashed circles, are: 1. lysophosphatidic acid, 2. lysophosphocholine, 3. PI; 4. PI(3)P; 5. PI(4)P; 6. PI(5)P; 7. phosphatidyletanolamine; 8. phosphatidylcholine; 9. spingosine-1-phosphate; 10. PI(3,4)P$_2$; 11. PI(3,5)P$_2$; 12. PI(4,5)P$_2$; 13. PI(3,4,5)P$_3$; 14. phosphatidic acid; 15. phosphatidylserine; 16. blank. The strip was incubated with human PAP at concentration 10 μg/ml.

(E) PI(3)P phosphatase activity of PAP. Phosphatase assays containing 0.01 μg/μl PAP with varying amounts of PI(3)P or buffer were incubated for 5 min at 37° C. and free phosphate was measured by malachite green assay. Initial velocities were calculated from these time courses and plotted against the respective substrate concentration.

Figure 2:
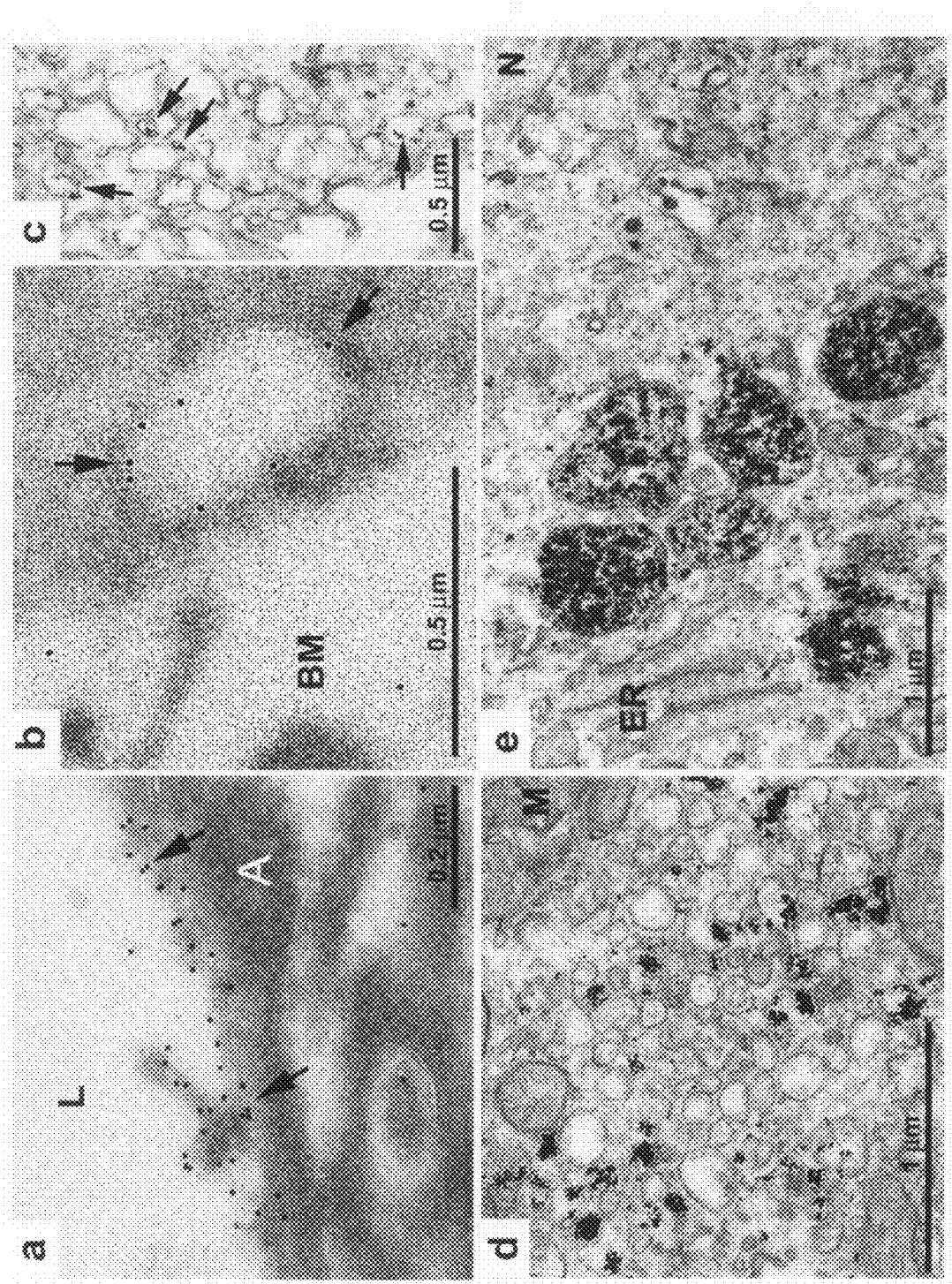

FIG. 2 shows the PAP found on (A) plasma membrane, (B) membrane-associated vesicles in mouse prostate, (C) caveosome-like vesicles, (D) early endosome-line vesicles and (E) lysosomes.

Figure 3:
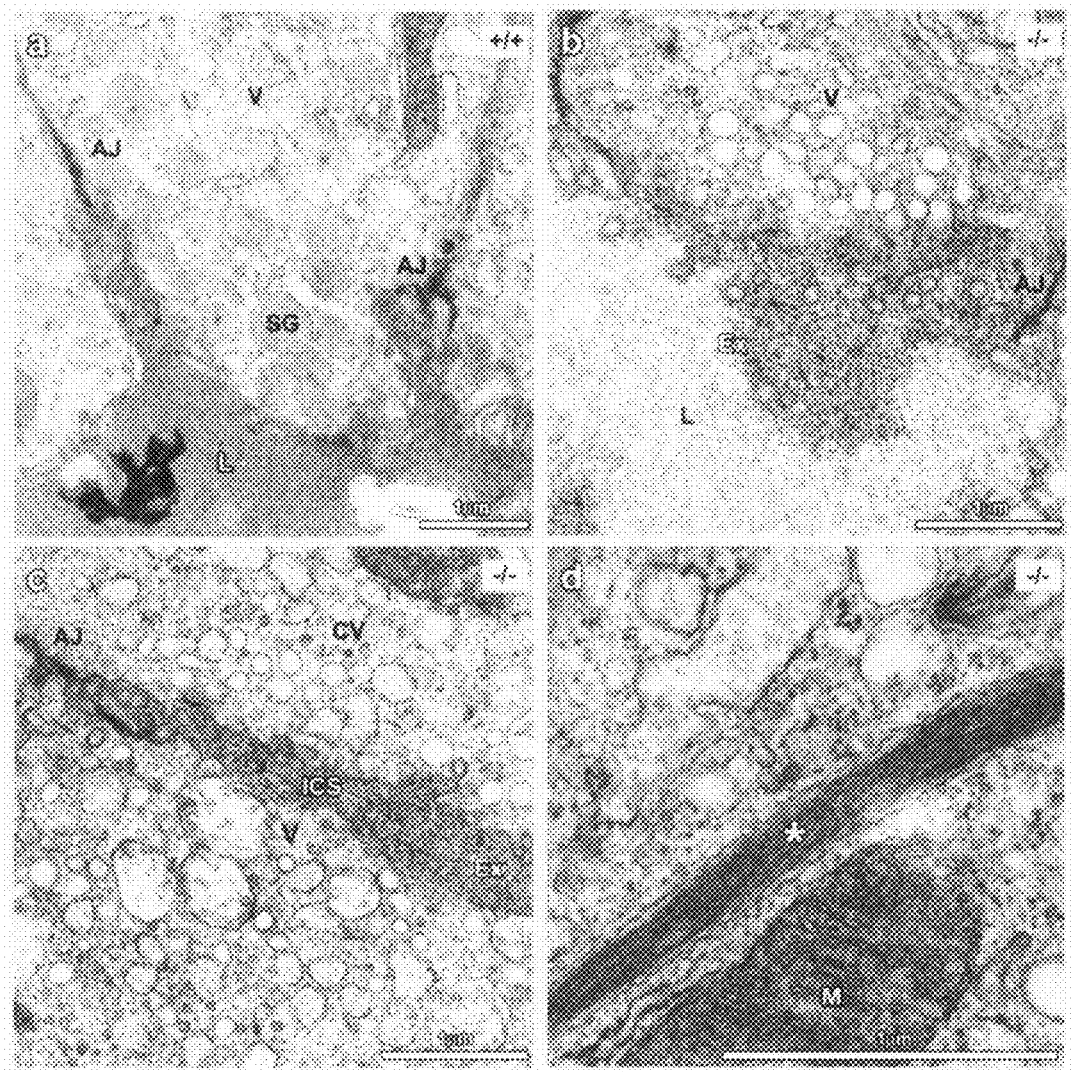

FIG. 3 shows the increased number of enlarged vesicles and increased apical and basolateral exocytosis-like secretion (A-D).

Figure 4:
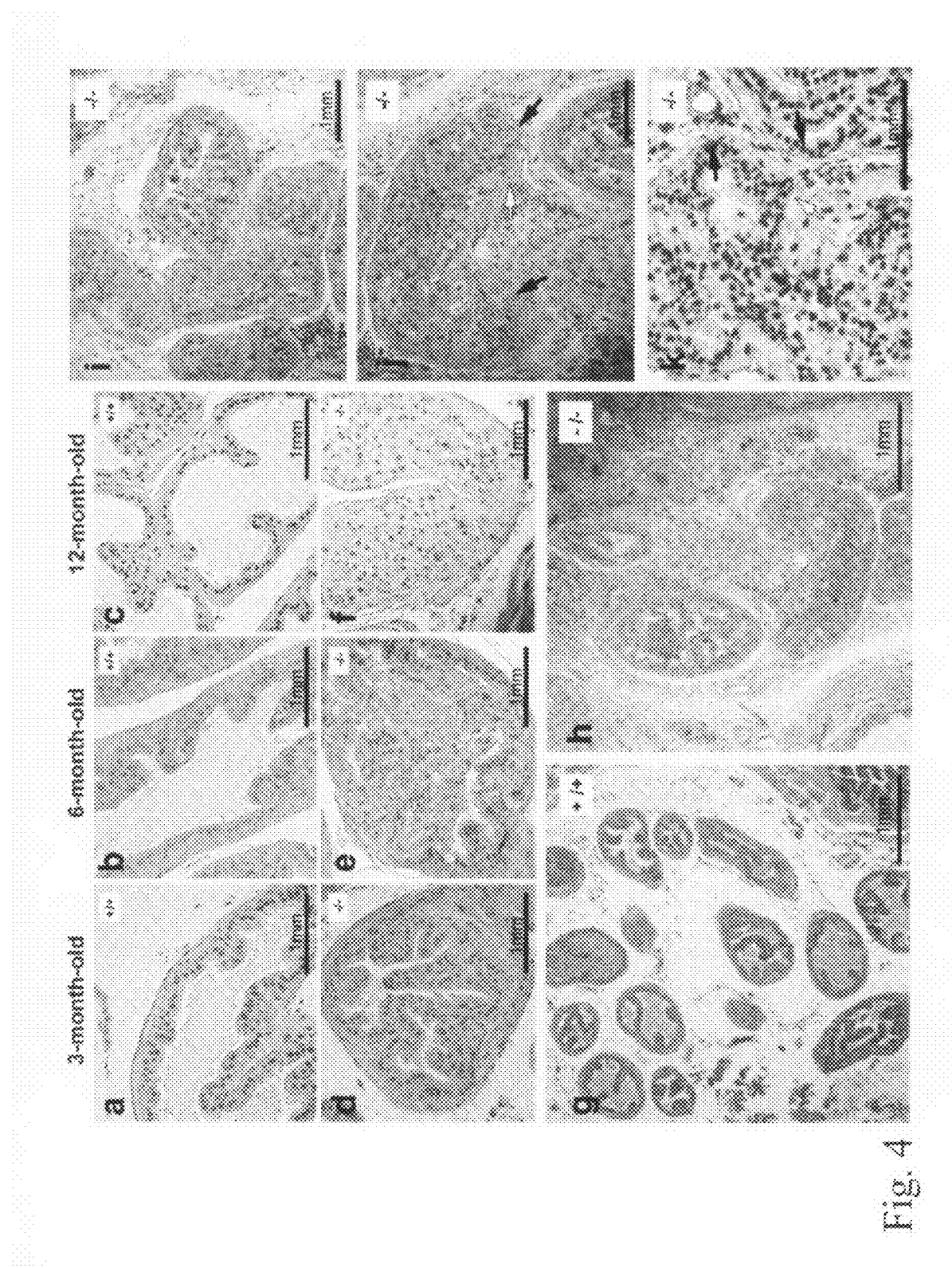

FIG. 4 shows gradual development of atypical changes (A-H).

Figure 5:
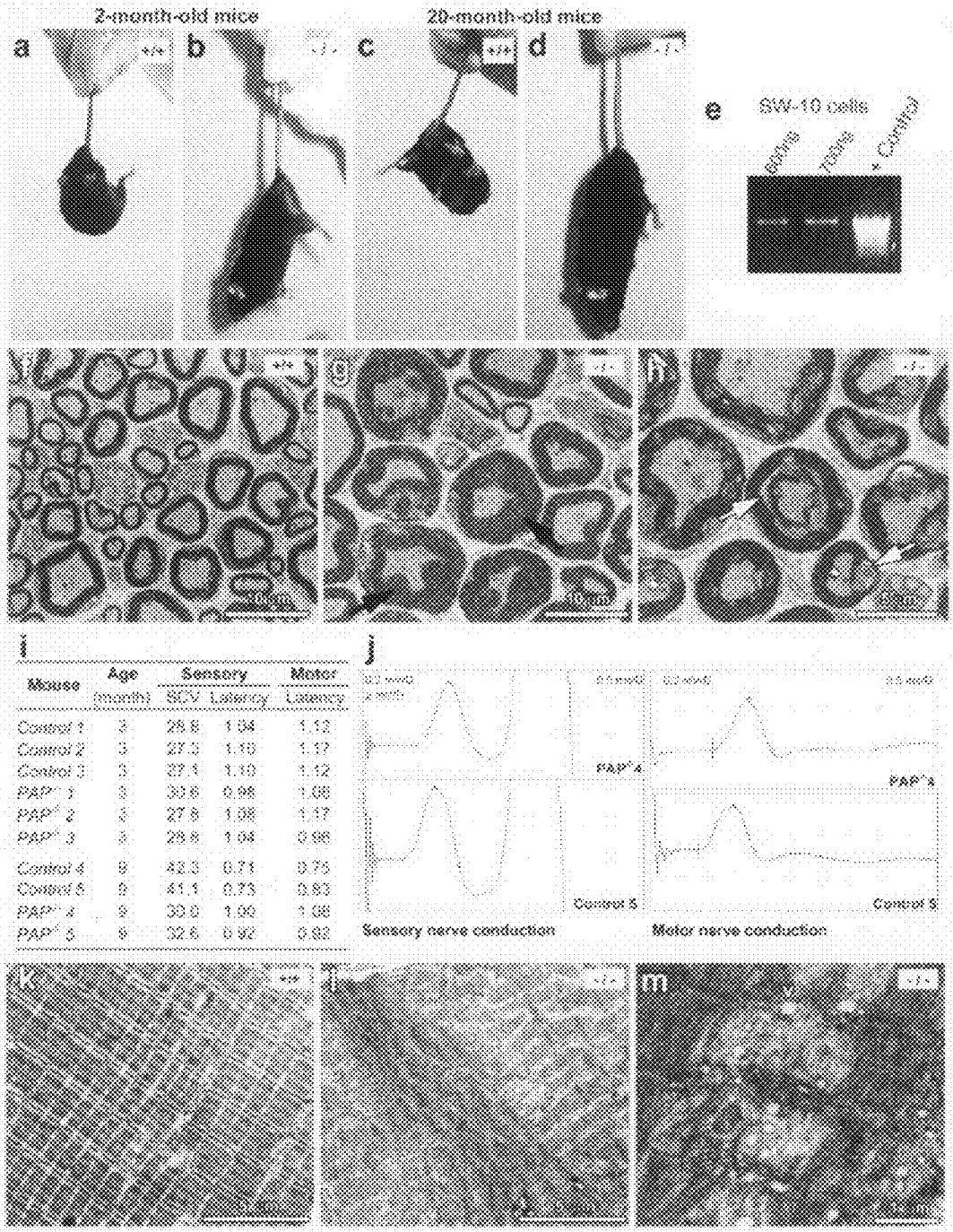

FIG. 5 shows how muscle weakness was detected in PAP$^{-/-}$ mice (A-D), impaired myelin formation (F-H), electrophysiological measurements of sensory and motor conduction on tail nerve (I,J) and disorganized fibers, inclusions and enlarged vesicles (L,M).

Figure 6:
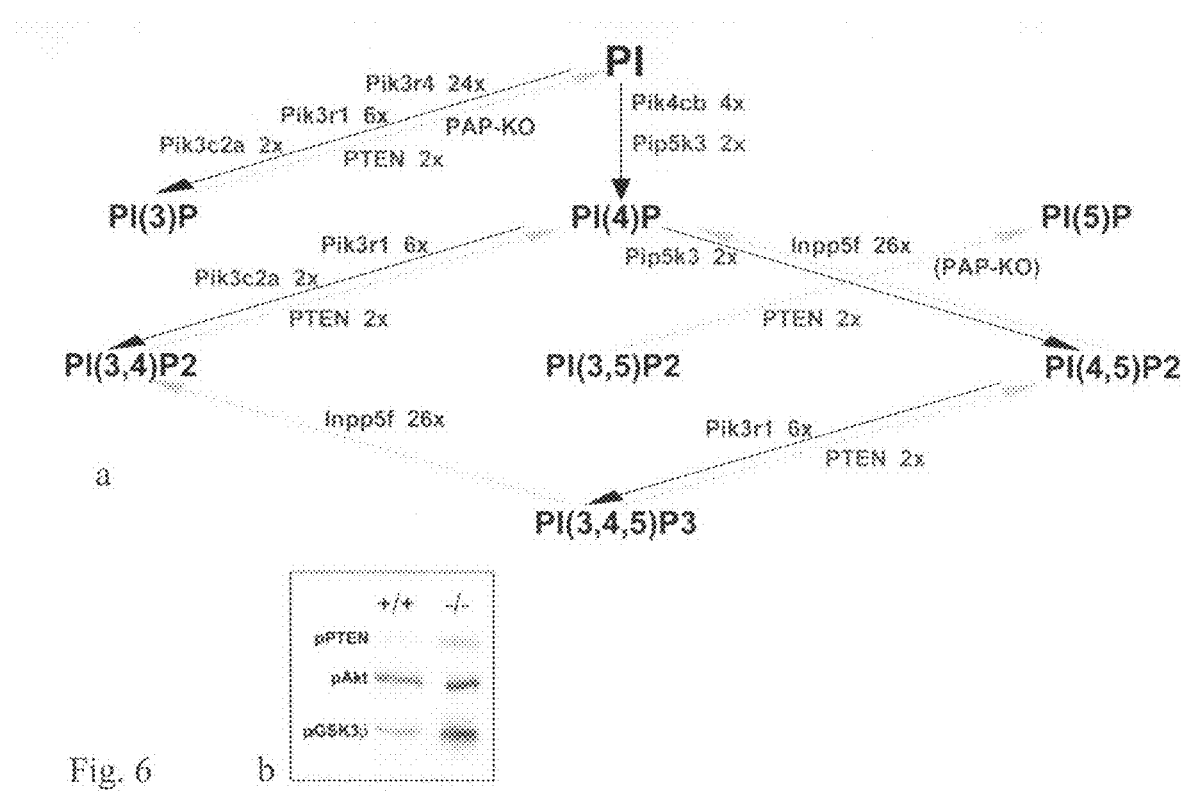

FIG. 6 shows changes in the gene expressions of PI-kinases, their adaptor proteins and PI-phosphatases (A) and Western blot results showing an increased amount of PTEN phosphorylated (B).

Figure 7:
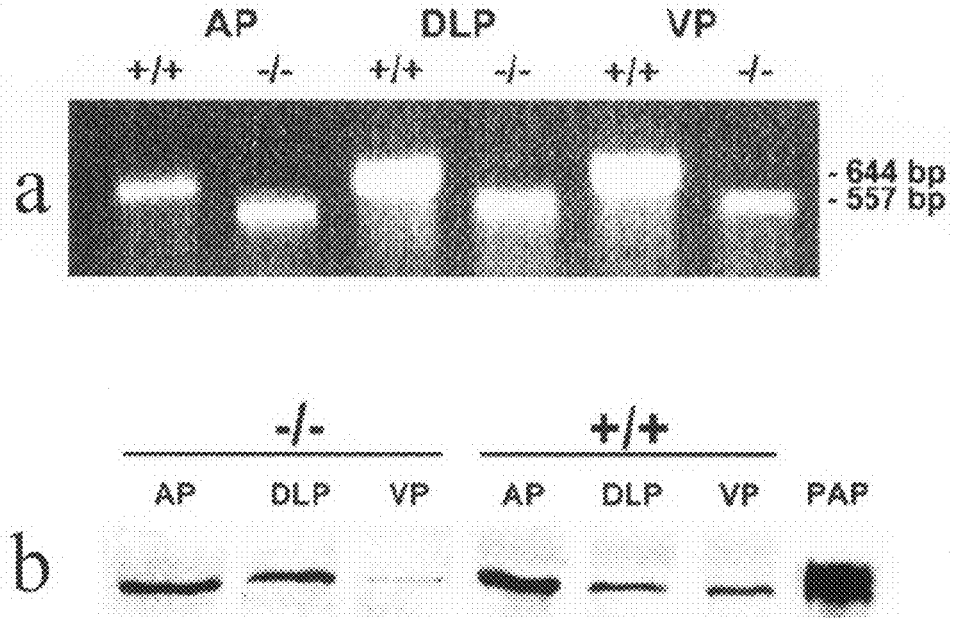

FIG. 7 shows the generation of PAP activity-deficient mouse. (A) The PAP gene product is expressed in every prostate lobe. Splicing out of exon 3 results in a gene product of 557 nt in PAP$^{-/-}$ mice. (B) Western blot analyses of PAP expression in different prostate lobes of PAP$^{+/+}$ and PAP$^{-/-}$ mice. The positive control is hPAP purified from semen.

Figure 8:
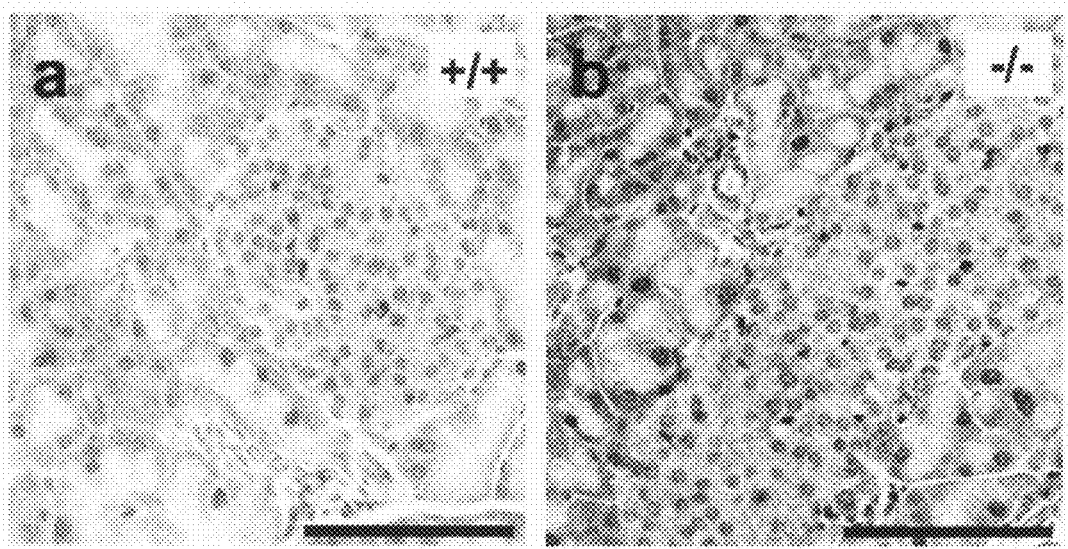

FIG. 8 shows that PAP is expressed in Langerhans islets. Immunostaining of pancreas with anti-PAP antibody of six-month-old PAP$^{+/+}$ and PAP$^{-/-}$ mice. Bar=1 mm.

Figure 9:
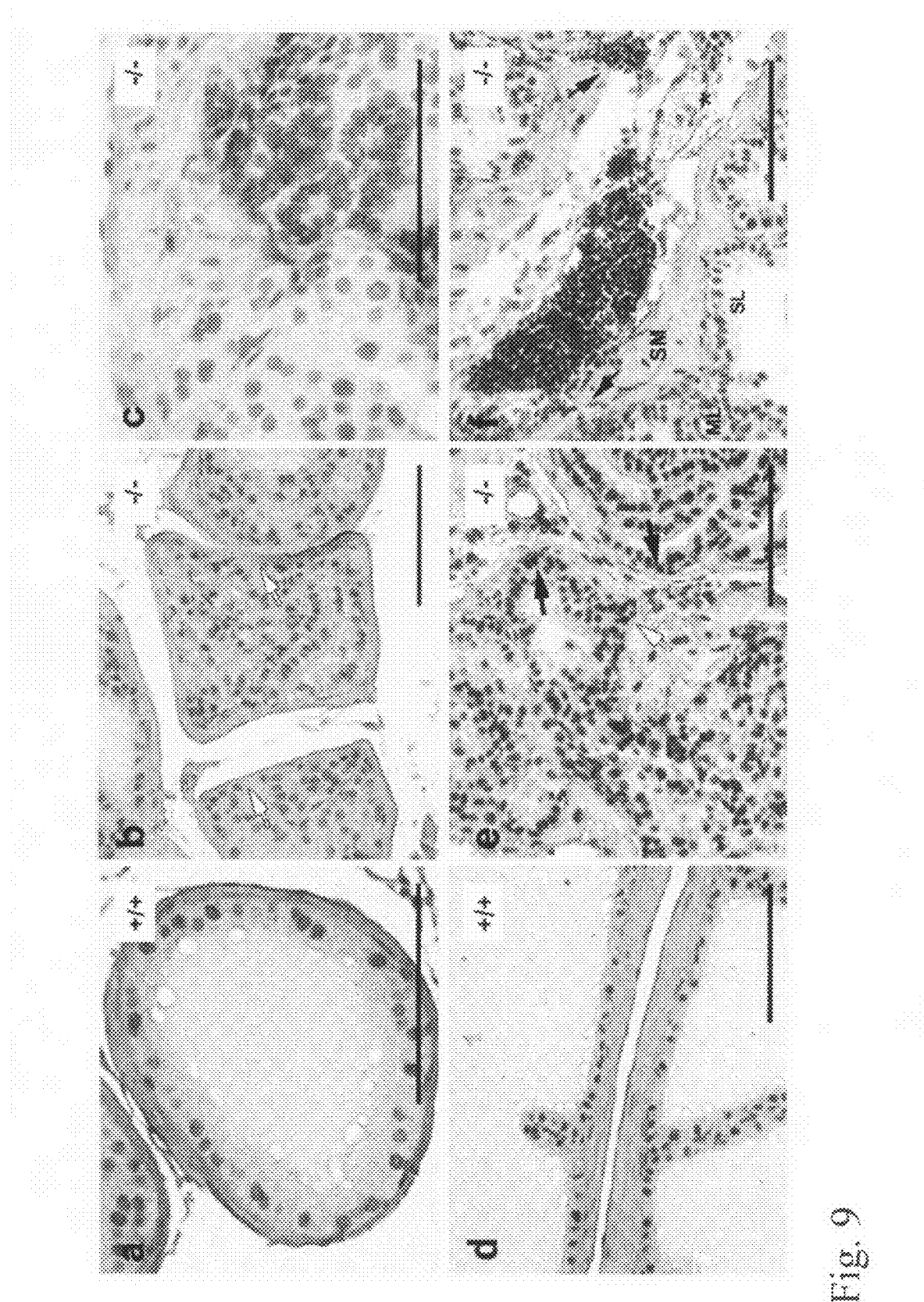

FIG. 9 shows smooth muscle α-actin staining of the fibromuscular sheath. (A,D) Normal fibromuscular sheath structures in the DLP and AP lobes of PAP$^{+/+}$ mice. (B) The fibromuscular sheath is thin and irregular and tends to break down in the DLP of a PAP$^{-/-}$ mouse. (C) Adenocarcinoma shows different stages of differentiation. (E,F) The fibromuscular sheath is losing its structure in the AP of a PAP$^{-/-}$ mouse. Epithelial cells are bulging against the fibromuscular sheath (white arrow), and cancerous cells are breaking through (black arrows). Epithelial cells are visible in a blood vessel (*). An inflammatory response can be detected. ML=multilayer epithelium, SL=single-layer epithelium, SM=smooth muscle. Bar=1 mm.

DEFINITIONS

"Knockout" as used herein refers to a process of purposely removing a particular gene or trait from an organism or cell. Generally a knockout is a site-specific integration that usually deletes an essential part of a gene of interest. Methods of making knockouts are generally known in the art, for example microinjection and targeted mutation methods. The knockouts of the present invention may be done with any known knockout methods, such as any heritable modifications of the PAP gene, as long as they result to substantial disruption of at least part of the PAP gene or an expression regulation region thereof resulting in substantial disruption of the original function of expressed PAP enzyme or the original function of PAP gene. In one embodiment the knockout is done by replacing a part of the PAP gene with an external nucleic acid molecule and introducing this modified gene into the genome of the animal to replace the original PAP gene. The knockout may also be done by removing the whole gene of interest.

The terms "substantially disrupted" or "substantially reduced" are herein intended to mean that substantially lower amount of normal PAP gene product is produced in cells or in organism when compared to normal cells or organisms. Preferably such lower amount refers to essentially undetectable amount of normal gene product. This type of mutation is generally called as a "null mutation" and an animal carrying such a mutation is also referred to as a "knockout animal". Correspondingly, when an animal cell is used the cell carrying such a mutation is referred to as "knockout cell".

The "decrease in activity" of the PAP as used herein refers to a decrease of total enzyme activity of said disrupted or substantially disrupted PAP gene product in certain cells. Said decrease in activity may be partial or the activity may be totally lost and it is sufficient to cause disorders related to PAP gene, such as described in the specification. Said decrease in activity may relate for example to reduced level of expressed PAP, for example if the promoter region of the PAP gene has been altered, or to disrupted structure or function of PAP enzyme. "Decrease in the activity of (expressed) PAP" refers not only to expressed PAP which has lower activity compared to normal PAP, but also to PAP which is expressed at lower levels than normally. This embraces also PAP which is substantially not expressed at all.

The "PAP gene" as used herein refers to any suitable prostatic acid phosphatase gene or homologue or derivative thereof. The PAP gene to be used in the present invention may be of any suitable origin, plant or animal, such as rat, mouse or human PAP gene. In one embodiment the human prostatic acid phosphatase (hPAP) gene is used to provide a model for investigating human PAP-related disorders. The human PAP gene may be inserted to another species, such as rat or mouse, or to a cell thereof, to provide a transgenic animal or cell model for investigating said disorders or diseases. Also PAP genes of other origins may be used, such as mouse PAP (mPAP) or rat PAP (rPAP). Generally any PAP gene from any suitable organism, which will produce, when expressed in a cell, a substantially functional PAP enzyme, may be used. Such PAP gene may be a homologue of a known PAP gene from certain species having insertions or deletions of amino acids, but still having sufficient homology with the original gene to produce substantially analogous PAP enzyme. Generally such homology is preferably at least 50%, more preferably 80% and most preferably 90% at amino acid level.

"Phosphatidylinositol phosphate" (PIP) refers to any phosphatidylinositol phosphate as described herein, such as phosphatidylinositol 3-phosphate PI(3)P, phosphatidylinositol 4-phosphate PI(4)P, PI(5)P, PI(3,5)$_2$, PI(4,5)P$_2$, PI(3,4,5)P$_3$ or corresponding soluble inositol phosphate (IP).

DETAILED DESCRIPTION OF THE INVENTION

To find out the physiological function of PAP, the inventor of the present invention simultaneously modeled, based on the conserved active site amino acid residues of PAP and *E. coli* phytase, inositol phosphates (IP) and phosphorylated phosphatidylinositols, collectively called phosphoinositides (PI), as substrates, studied the subcellular localization of PAP, and generated a PAP activity-deficient mouse model by deleting the 3rd exon of the PAP gene. The findings showed that PAP is a phosphatidylinositol 3-phosphate [PI(3)P] phosphatase on the endosomal pathway, and that knockout of PAP activity results in a changed PI-kinase/phosphatase cascade favorable for PI(4,5)P$_2$ accumulation, which is causative of altered G-protein signaling and vesicular/membrane trafficking and of prostate adenocarcinoma, myopathy and neuropathy.

The current invention utilizes knockout animals and cells wherein at least one allele of an endogenous prostatic acid phosphatase (PAP) gene is functionally disrupted in somatic and/or germ cells. Said animals or cells may be heterozygous or, preferably, homozygous for the PAP knockout.

Animals to be used in the animal model of the present invention include any suitable non-human animals, such as vertebrates, or more particularly mammals. The term animal includes an individual animal in all stages of development, including embryonic and fetal stages. In one embodiment of the invention the animal is a rodent, such as mouse or rat, which are generally used as similar applications may be adapted to both species. The cells to be used include any suitable cells, from plants or animals, for example ones derived from the animal described above or human cell lines.

The disruption may be made to exon 3 of the PAP gene. This is preferred because exon 3 is involved with PAP activity. This will ensure that the activity of the PAP enzyme will be abolished. Said exon 3 may be knocked out totally or its function may be decreased partially. However, similar disruptions or knockouts may be also made to another suitable part of PAP gene, for example by introducing deletions or insertions of nucleic acids to obtain the defective PAP. The PAP gene may also be totally removed. Said disruption may also refer to the level of expressed gene product.

Said disruption may be introduced into said prostatic acid phosphatase gene by replacing at least part of it with an external nucleic acid sequence. One example of such external nucleic acid sequence is the commonly used neo cassette.

Said prostatic acid phosphatase gene may be originated from different species, such as human, mouse or rat prostatic acid phosphatase gene or homologue thereof, or it is a recombinant PAP gene.

Said external nucleic acid molecule used for replacing part of the PAP gene may be any suitable nucleic acid molecule containing suitable nucleic acid sequence which is able to decrease the activity or level of expressed prostatic acid phosphatase when inserted to the PAP gene, for example at the location of exon 3. Targeting to generate a null or mutated allele is usually accomplished by insertion of a selectable marker into a gene causing disruption of splicing, promoter function, or reading frame, with or without deletion of some of the gene. One commonly used selectable marker gene for making knockouts is the neo gene, which confers resistance to the antibiotic neomycin. Also other suitable sequences may be used.

One embodiment of the present invention provides methods of screening a compound, such as a drug candidate, for a therapeutic effect, comprising: a) exposing the knockout animal or cell to a compound and b) determining the response of the animal or cell to the compound. In certain embodiments, a change in response compared to the response of a knockout animal or cell not exposed to the compound indicates the response to the compound. Such control animal may be exposed for example to placebo or other compound. In one embodiment the response of a knockout animal or cell is compared to one of a wild type animal. In other embodiments, the knockout animals or cells are examined directly without comparison to a wild-type animal. Such methods are generally well known in the art. Said therapeutic effect is against a disorder related to prostatic acid phosphatase. Non-limiting examples of such disorders are prostatic atypical hyperplasia, prostatic intraephitelial neoplasia, carcinoma and other disorders related to phosphorylation/dephosphorylation or transport of phosphatidylinositol 3-phosphate (PI(3)P). As PAP is now known to reduce the amount of PI(3)P, said disorder may be associated with the PI(3)P metabolism and related mechanisms, such as insulin response, lipid metabolism, growth factor response, cell division, apoptosis etc., which are regulated by PI(3)P. Said diseases and disorders include prostate, bladder and pancreatic cancer, myopathy (myodegeneration) and neuropathy (neurodegeneration). A compound found with the method of the invention may be used as medicament for treating the disorders disclosed herein. Non-limiting example of such compound may be a compound acting as an enhancer for the expression of PAP.

One embodiment of the present invention provides diagnostic methods wherein the increased level of PI(4,5)P$_2$ measured from a sample is used to indicate the presence of a disease or disorder related to unbalanced phosphatidylinositol phosphate cascade or signaling pathway related to prostatic acid phosphatase as described herein. A person skilled in the art can easily select a method for measuring the level of PI(4,5)P$_2$ and also compare the measured values to normal reference values in order to make the diagnosis. The general level of PI(4,5)P$_2$ defined from a healthy reference group may be used as reference when defining said increased level of PI(4,5)P$_2$. Said sample may be in vitro or in vivo sample, such as one taken from a tissue suffering from suspected disorder or disease or the like. In one embodiment the increased ratio of PI(4,5)P$_2$/PI(4)P is further used to indicate the presence of said diseases or disorders. Normally this ratio is about 1, but in pathological conditions the level of PI(4,5)P$_2$ is increased and the ratio is substantially over 1, for example about 2, 3 or 4.

One embodiment of the present invention provides methods for treating said diseases or disorders related to PAP by gene therapy and other methods to restore the activity of PAP. A compound affecting to the expression or effect of PAP may be administered to tissues or cells of a patient suffering a condition or disorder related to PAP, as described above. Also gene therapy affecting to or restoring the activity of PAP may be given to such patient. The gene therapy preferably restores at least part of the PAP activity. Suitable genes to be used in such gene therapy include any suitable PAP gene or nucleotide vector of the invention as described herein. The gene therapy or other treatment may be administered to the patient for example by injection to target, such as to prostate or by prostate artery, as a virus vector. Such gene therapy methods are generally well known in the art and a person skilled in the art can choose a suitable method for the treatment. Examples of commonly used virus vectors which may be used to carry the PAP gene include baculo, adeno and lenti viruses (see e.g. Airenne et al.: "Baculovirus-mediated Gene Transfer: An Evolving New Concept", Templeton N S, ed. Gene and Cell Therapy, 181-197, New York, Marcel Dekker, 2004; Kost et al.: "Baculovirus as versatile vectors for protein expression in insect and mammalian cells, Nature Bio-technology 2005:23, 567-575).

To find out the physiological function of PAP in the prostate PAP knockout (KO) mouse model was generated by deleting the 3$^{rd}$ exon of the mPAP gene. The present inventor found out that PAP is PI(3)P-lipid phosphatase, regulates PI(3)P membrane traffic, and its inactivation is causative for prostate cancer. The corresponding publication (Vihko P T, Quintero I, Ronka A E, Herrala A, Jantti P, Porvari K, Lindqvist Y, Kaija H, Pulkka, A, Vuoristo J, et al. 2005 Prostatic acid phosphatase (PAcP) is PI(3)P-phosphatase and its inactivation leads to change of cell polarity and invasive prostate cancer. p 1328 (#5239) *Proceedings of the AACR: 96th Annual meeting*, Anaheim, Calif.) is incorporated herein by reference.

Discussion

In this study the physiological substrate and function of PAP as a regulator of membrane traffic is described. The study shows that PI(3)P is not only localized in early endosomes and multivesicular bodies, but together with PAP it has a role in the apical membrane and in cell-cell interactions.

The PAP$^{-/-}$ mouse is the model for invasive prostate cancer both in AP and DLP lobes. Gene expression and subcellular changes are detected long before histological changes. These results clearly show that together PAP and its physiological substrate PI(3)P have a crucial function in the prostate gland and that PAP is a tumor suppressor.

PAP is a Novel PI(3)P-Phosphatase and Allosterically Regulated

Phosphatidylinositol (PI) constitutes about 8% of all phospholipid in mammalian cells. It is present in the cytoplasmic leaflet of various cellular membranes. Activation of cell membrane receptors by extracellular stimuli leads to generation of second messengers from phosphatidylinositol by specific kinases (PI3Ks) phosphorylating the inositol headgroup of PI in cells in the 3-, 4- or 5-position. PI and its phosphorylated derivates recruit effector proteins to specific subcellular localizations and contribute to their activity. PI(3)P, PI(4)P, PI(3,5)$_2$ and PI(4,5)$_2$ have important, albeit not completely elucidated roles both in regulated and constitutive membrane traffic. The differential intracellular distribution of PIPs can be achieved by localized synthesis and degradation resulting from restricted distribution of PI-kinase and PI-phosphatase isoforms. Many of these kinases and phosphatases are cytosolic enzymes, and their targeting to different intracellular domains is not completely elucidated. It is however known to often involve small GTPases and GTP-binding proteins.

Known PI3Ks can be divided into three classes. In vitro class I and class II PI3Ks utilize PI, PI(4)P, and PI(4,5)P$_2$ as substrates, with the preference of class I PI3K for PI(4,5)P$_2$ and class II PI3K for P is. Class III PI3Ks only use P is as a substrate in vitro, and are believed to be responsible for the generation of the majority of the PI(3)P in cells. Differing from the cytosolic localization of class I PI3Ks, class II enzymes are predominantly membrane-bound. PI3K-C2β has a carboxyl terminal phospholipid and Ca$^{2+}$ binding domain C2 and it has been demonstrated in nuclear membranes and the nucleus.

It is described herein that PAP is a novel PI(3)P-phosphatase. PI-phosphatases can be divided into different groups based on their favored substrate: 3- and 4-phosphatases from the CX$_5$R families and type II 5-phosphatases. CX$_5$R has been identified as an active site motif of the protein tyrosine phosphatase family. Only a few tyrosine phosphatases have been shown to possess inositol lipid phosphatase activity. The best-known PI(3)P-phosphatases so far are myotubularin (MTM) and phosphatase and tensin homolog deleted on chromosome 10 (PTEN).

Allosteric regulation is characteristic of PI-phosphatases. Kinetic analysis of PAP with PI(3)P showed that plots of initial reaction velocity as a function of substrate concentration are not hyperbolic, and hence PAP does not obey Michaelis-Menten kinetics, but sigmoidal curves were obtained. This suggests an allosteric regulation mechanism. From other lipid phosphatases PTEN and phosphatases of the myotubularin family have been reported to be regulated through allosteric mechanism by the end product or by other PIP. When PTEN is hydrolyzing PI(3,4,5)P$_3$, the end product, PI(4,5)P$_2$, regulates the phosphatase activity of PTEN in vitro through an allosteric mechanism. MTM1 and MTM6 hydrolyze mostly PI(3)P and PI(3,5)P$_2$ in vitro, and PI(5)P has been reported to have a positive feedback effect on both reactions. On the contrary to PTEN and myotubularins, which besides their favorite substrate, hydrolyze other PIP-compounds, although less effectively, PTEN-like phosphatase (PLIP) hydrolyzed specifically only PI(5)P, and the activity showed a hyperbolic dependence on substrate concentration. However, critical time points between 0 and five minutes were not examined and the possibility of allosteric regulation by other PIPs can not be excluded.

Searches with SMART and InterPro Scan programs were used to find out these domains in the PAP sequence. In contrast to MTM and PTEN, the only domain found in PAP was the acid phosphatase domain, which did not include the PTP active site CX$_5$R motif, suggesting that PAP has additional differences compared to other known PI(3)P-phosphatases. In addition to the acid phosphatase domain, lysosome targeting, caveolin and cholesterol binding domains were found (Table 1).

TABLE 1

Putative interaction I recognition motifs in PAP protein

| Residues in PAP | Sequence | Consensus sequence | Interaction/recognition |
|---|---|---|---|
| 255-259 | KSRLQ (SEQ ID NO: 3) | K-X-X-X-Q | lysosomal |
| 272-276 | KRATQ (SEQ ID NO: 4) | K-X-X-X-Q | lysosomal |
| 18-25 | FLFLLFFW (SEQ ID NO: 5) | φ-X-X-X-X-φ-X-φ | caveolin |
| 89-97 | YRKFLNESY (SEQ ID NO: 6) | φ-X-X-φ-X-X-X-X-φ | caveolin |
| 81-90 | LGEYIRKRYR (SEQ ID NO: 7) | L/V-X(1-5)-Y-X(1-5)-R/K | cholesterol |
| 153-159 | LLYLPFR (SEQ ID NO: 8) | L/V-X(1-5)-Y-X(1-5)-R/K | cholesterol |
| 241-253 | LSLLSLYGIHKGK (SEQ ID NO: 9) | L/V-X(1-5)-Y-X(1-5)-R/K | cholesterol |
| 315-322 | LTELYFEK (SEQ ID NO: 10) | L/V-X(1-5)-Y-X(1-5)-R/K | cholesterol |
| 327-332 | VEMYYR (SEQ ID NO: 11) | L/V-X(1-5)-Y-X(1-5)-R/K | cholesterol |

φ represents residue of F, W or Y, X represents any amino acid, and X(1-5) one to five residues of any amino acids.

PAP Knockout Mouse Model as Prostate Cancer Model

Mouse DLP is considered most similar to the human peripheral zone, where most detected cancers arise. Mouse AP is considered analogous to the human central zone around the urethra, where cancers exist and are detected by transurethral resection. Mouse VP has no human homolog and the human transitional zone has no mouse homologue.

Mouse prostate cancer models have been created either via transgenic or knockout approaches. So far, the transgenic adenocarcinoma mouse prostate (TRAMP) (Greenberg et al., 1995, Proc. Natl. Acad. Sci. U.S.A. 92, 3439-3443; Garabedian et al., 1998, Proc. Natl. Acad. Sci. U.S.A. 95, 15382-15387) and the PTEN conditional knockout mouse prostates (Wang et al., 2003, Cancer Cell. 4, 209-221; Backman et al., 2004, Proc. Natl. Acad. Sci. U.S.A. 101, 1725-1730) progress beyond the PIN lesion into invasive prostate cancer. Total KO of PTEN is lethal. Only PTEN KO-mouse mimics genetic alterations found in human prostate cancer, since TRAMP is the SV40 T antigen model, which has high neuroendocrine differentiation potential. In PTEN$^{-/-}$ mice invasive prostate cancer develops by nine weeks of age, and adenocarcinoma was found in all lobes. However, only results of DLP cancer were shown.

In the PAP$^{-/-}$ mouse model of the present invention progressive development of prostate cancer was detected in both AP and DLP. Invasive cancer was detected in both AP and DLP, but not in VP, by 6-24 months, and all males developed it. Changes were constant in different animals. Knockout of one single prostate gene led to progressively growing prostate cancer. Invasive cancer developed via atypic hyperplasia, low-grade and high-grade PINs, and the development of histologically manifest cancer was rather slow, as is also the case with human prostate cancer. However, changes both at gene expression and subcellular level took place early after sexual maturation in PAP$^{-/-}$ mice prostates.

The present results show that PAP is an important regulator of the function of the prostate gland and its inactivation is causative for prostate cancer. The conclusion is that PAP is a novel tumor suppressor. The PAP$^{-/-}$ mouse model of prostate cancer will be beneficial for science and patients.

Examples

Figure 1:
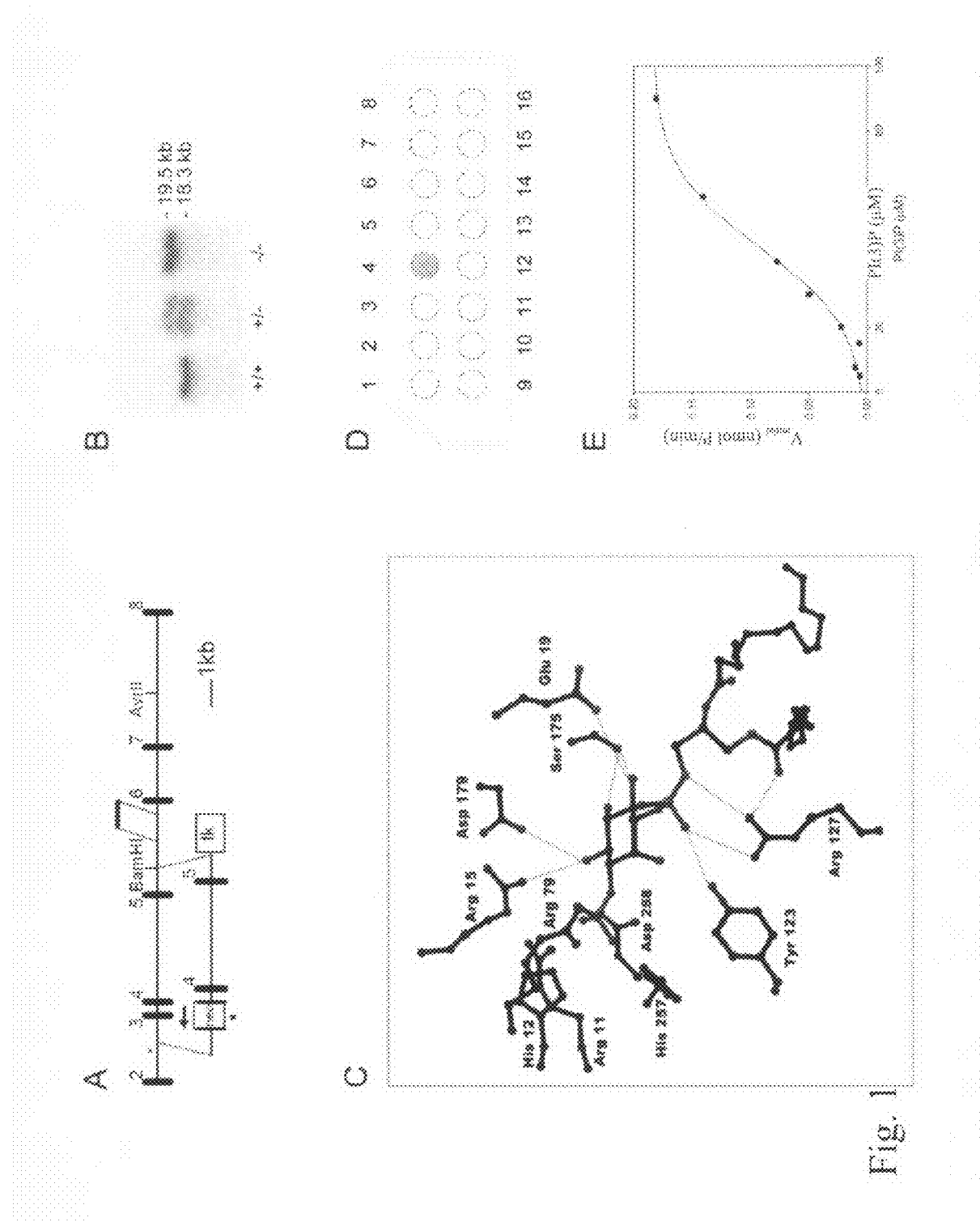
FIG. 1 shows the generation of PAP$^{\Delta3/\Delta3}$ deficient mouse.

To demonstrate the idea of the current invention a knockout mouse model was generated, in which model the activity of PAP has been removed by replacing the exon 3 of mPAP gene with neo cassette, and targeting was confirmed with Southern blot (FIG. 1A,B). The PAP expressed in the prostate of PAP$^{-/-}$ mice was catalytically inactive but immunologically reactive (FIG. 7A,B). PAP knockout mice are fertile and currently there exist −/− mice with homogenous background to C57BL/6 mouse strain. The removal of PAP activity inflicts changes in the mouse prostate, mainly in dorso-lateral and anterior lobes. Phenotypic changes can already be observed in heterozygotes.

The experiments described below are conducted with mice, but as a person skilled in the art knows, also other suitable animals may be used, for example rats. The PAPs and the functions thereof described herein are similar among different species.

PAP is PI(3)P-Lipid Phosphatase

The modeling revealed that PAP binds PI(3)P perfectly. Only PI with P in position 3 was able to align for hydrolysis, at the same time giving good interaction to the inositol ring and the 1-phosphate group (FIG. 1C). Introduction of a further phosphate group on the inositol ring introduced unfavorable interactions, and in some instances steric hindrance. In addition, hydrogen bond interactions with Tyr123, Arg127 and Ser175 are specific to prostatic acid phosphatase; these residues are not conserved in lysosomal acid phosphatase.

The interaction between PAP and PI lipids was investigated using protein overlay assay. PAP binds strongly only to PI(3)P (FIG. 1D). PAP showed no affinity to the other lipids tested: lysophosphatidic acid, lysophosphocholine, PI, PI(4)P, PI(5)P, PI(3,4)P$_2$, PI(3,5)P$_2$, PI(4,5)P$_2$, PI(3,4,5)P$_3$, phosphatidylethanolamine, phosphatidylcholine, sphingosine-1-phosphate, phosphatidic acid, or phosphatidylserine. This shows that PI(3)P is a principal substrate for PAP.

To confirm that PAP hydrolyses PI(3)P the lipid phosphatase activity of PAP towards PI(3)P was studied. Results indicated that PAP utilizes PI(3)P as a substrate (FIG. 1E). Being sigmoidal, the kinetic curve was inconsistent with Michaelis-Menten kinetics.

PAP is found on plasma membrane (FIG. 2A) and is membrane-associated in vesicles in mouse prostate (FIG. 2B). IEM studies with LNCaP cells showed PAP to be topologically present on the PI pathway: caveosome-like vesicles (FIG. 2C), early endosome-like vesicles (FIG. 2D), and lysosomes (FIG. 2E).

PAP-Deficient Mice Develop Adenocarcinoma of Prostate, Myopathy, and Neuropathy

PAP has so far also been found to be expressed in lactating mammary gland, salivary gland, Schwann cells, muscle, liver, lung, kidney, spleen, thymus, bladder, Langerhans islets (FIG. 8) and granulocytes. In TEM studies, prostate cells of two-month-old PAP-deficient mice had lost their microvilli and single-layer columnar epithelial structure, characteristic of the loss of cell polarity. The increased number of enlarged vesicles and increased apical and basolateral exocytosis-like secretion were seen with filament structures stacking inside the epithelial cells of PAP$^{-/-}$ prostates (FIG. 3A-D). Gradual development of atypical changes, e.g. low-grade prostatic intraepithelial neoplasia (PIN), high-grade PIN, and adenocarcinoma involving all epithelium of AP and DLP lobes, in PAP$^{-/-}$ mice was observed, and evident nuclear variation and disorders of cellular orientation were present (FIG. 4A-H). No premalignant or malignant changes were seen in the VP lobes of PAP$^{-/-}$ mice. Bulging of epithelial cells into the fibromuscular sheath and invasion of these cells into stroma lacking cohesion and intra-epithelial vascularization were seen (FIG. 4K, 9).

When the specimens analyzed at the ages of three and six months were compared, apoptosis was significantly decreased at six months in DLP (p=0.04) and AP (p=0.008), whereas proliferation was significantly increased in both DLP (p=0.002) and AP (p=0.004). Muscle weakness was detected in PAP$^{-/-}$ mice (FIG. 5A-D). Impaired myelin formation was already detected at the age of two months in the sciatic nerve of PAP$^{-/-}$ mice (FIG. 5F,G). There appeared tomacula, hypermyelination of myelin sheath associated with myelin outfoldings, and active myelin breakdown (FIG. 5G,H). Electrophysiological measurements of sensory and motor conduction on the tail nerve did not show any changes in sensory conduction velocity (SCV), latency or amplitude values between PAP$^{-/-}$ and PAP$^{+/+}$ mice at the age of three months. In nine-month-old PAP$^{-/-}$ mice, however, SCV and motor latency were clearly reduced (FIG. 5I,J). Changes in the sensory amplitude of nine-month-old mice indicated probable axonal degeneration. These findings are compatible with demyelinating motorsensory neuropathy.

In the skeletal muscle of PAP$^{-/-}$ mice, typical myopathic changes in the tubular array structure were evident in TE micrographs. Disorganized fibers, inclusions, and enlarged vesicles could be seen in two-month-old PAP$^{-/-}$ mice (FIG. 5L,M), and the changes progressively increased.

Inactivation of PAP Alters the Expression of Genes in Phosphatidylinositol Phosphate Metabolism Microarray analyses revealed changes in the gene expressions of PI-kinases, their adaptor proteins, and PI-phosphatases (FIG. 6A). Genes related to kinases phosphorylating the inositol ring of PI and related compounds at the 3-position showed both upregulation and downregulation. The expression of Pik3c2a, encoding class II PI(3)K was increased (+2.3×). The genes for adaptor proteins, Pik3r1 of class I enzyme and Pik3r4 of class III enzyme, were downregulated −5.7× and −24×, respectively.

The PI(3)P, PI(3,4)P$_2$, and PI(3,4,5)P$_3$ are all dephosphorylated by PTEN. In PAP$^{-/-}$ prostates, Pten was upregulated (+2.1×). Extensive downregulation of the gene for Inpp5f (−26×) dephosphorylating PI(4,5)P$_2$ and PI(3,4,5)P$_3$ was detected. At the same time, the gene for Pip5k3, which phosphorylates PI to PI(4)P and further to PI(4,5)P$_2$, was upregulated (+2.5×). The expression of the PI4K-encoding gene, Pik4cb, was however decreased (−4.0×). Decreased Inpp5f expression increases PI(4,5)P$_2$ production, which leads to the generation of the second messengers IP3 and DAG by phospholipase C(PLC). There was no change in the expression of PLC-encoding genes, whereas the genes encoding Ppap2a and Ppap2b, which are enzymes converting phosphatidic acid (PA) to DAG, were substantially down-regulated (−39× and −11× respectively), presumably as a counteraction to increased DAG, resulting in an increase of PA. DAG-connected prostaglandin metabolism was also changed. Phosphatidylcholine (PC)-specific phospholipase D (PLD) activity regulates the formation of PA, which is a potent activator of type I PI-kinase catalyzing the phosphorylation of PI(4)P to PI(4,5)P$_2$. PLD is positively regulated by protein kinase C (PKC), Arf6, and PI(4,5)$_2$, which, in the case of PLD1, also localizes the enzyme to the plasma membrane. The expression of PKC genes was not changed in the microarrays, but the expression of Arf6 was downregulated −7.0×. The Ywhae gene for tyrosine-3 monooxygenase was down-regulated −9.8×. Ywhae belongs to 14-3-3 proteins, which are known to inhibit PKC. Elevated IP3 production gives rise to induced release of Ca$^{2+}$ from the endoplasmic reticulum and further effects through Ca$^{2+}$ effector proteins. The genes for several calcium-modulated proteins had changed expression as follows: Calm1 (calmodulin1) −4.0×, Camk1 (calcium/calmodulin dependent protein kinase I) −12×, S100A6 (S100 calcium binding protein A6 (calcyclin)) −5.3×, and Atp2c1 (ATPase, Ca$^{2+}$-sequestering) −32×.

G-Protein/Small G-Protein Signaling, Vesicular/Membrane Trafficking, and Cytoskeletal Organization are Changed PIs play a key role in signal transduction, cytoskeleton remodeling, cell migration, and vesicular/membrane trafficking. Changes in the PI-kinase/phosphatase cascade affect the expression of their regulators and effectors, such as small GTPases (Ras, Rho, Rab, Arf and Ran). Ras GTPases lead to alterations in gene transcription, Rhos regulate the actin cytoskeleton, Rab and Arf family GTPases control the formation, fusion, and movement of vesicular traffic between the different membrane compartments of the cells, Rans regulate both microtubule organization and nucleocytoplasmic protein transport.

A remarkable group of downregulated small G-protein genes were detected: those involved in endocytosis, sorting, and recycling of early/late endosomes and exocytosis: Rab4a (−4.6×), Rab5a (−3.7×), Rab11 (−4.0×), Rab18 (−4.3×), or in membrane transport in the early secretory pathway: Rab2 (−4.3×) and between the Golgi and endosomes: Rab14 (−2.5×). Arf6 (−7.0×) also plays a role in vesicular recycling and is essential in the internalization of most GPCRs, i.e. α2-adrenergic receptor (Table 2). Trim, which is also a member of the Arf family and known to be an activator of PLD and active in the movement of intracellular transport vesicles, was downregulated (−9.8×). There was a notable decrease of Gabarapl1 (−37×), which acts via vesicle transport on movement and the sorting of gamma-aminobutyric acid receptors (Gaba receptors) and as a tumor suppressor in breast cancer, and Picalm (−5.3×), which functions as an endocytic accessory protein including endocytic events at synapses. The regulator of G-protein signaling, Rgs2, which controls G αq, PLC, and AC, was strongly downregulated (−32×). The genes effective in the IGF-1 and EGF response, Iqgap1 (−4.6×), Cdc42 (−4×), and Rhoq (−3.2×), were also downregulated. Tumor suppressors, including Rap1b (−4×), Pfn1 (−3.5×), and Rhob (−2.6×), were affected.

Myo1b (−44×) is a calmodulin- and actin-associated myosin molecular motor also present in microvilli, which disappeared in the epithelial cells of PAP$^{-/-}$ prostates. Tpm1 (−42×), which induces stress fibers and functions as a tumor suppressor, Enah (−28×), actin-binding proteins, Spink3 (−119×), which is essential for the maintenance of the integrity of acinar cells, and Dnajb6 (−45×), a regulator of filament organization, are all downregulated. Microtubules constitute an important part of the cytoskeleton and are functionally involved in mitosis, membrane traffic, and cell movement. Microtubule-dependent motor proteins, such as Kif21a (−37×), Rp2h (−30×), and the cell adhesion and polarity regulators Rds (−6×), Cdc42 (4×), and Rac1 (−3×), were downregulated as well.

TABLE 2

Notably changed genes of PAP $^{-/-}$ prostates at the age of two months

| Accession number | Gene title | Change |
|---|---|---|
| Downregulated in G-protein signaling and vesicular trafficking pathways | | |
| NM_008247 | Phosphatidic acid phosphatase 2a; Ppap2a | 39 |
| NM_020590 | Gamma-aminobutyric acid receptor-associated; Gabarapl1 | 37 |
| NM_009061 | Regulator of G-protein signaling 2; Rgs2 | 32 |
| NM_080555 | Phosphatidic acid phosphatase 2b; Ppap2b | 11 |
| NM_030731 | Tripartite motif protein 23; Trim23 | 9.8 |
| NM_009536 | Tyrosine 3-monooxygenase activation protein, epsilon; Ywhae | 9.8 |
| XM_203999 | Rap guanine nucleotide exchange factor (GEF) 2; Rapgef2 | 8.6 |
| NM_053100 | Tripartite motif protein 8; Trim8 | 7.5 |
| NM_007481 | ADP-ribosylation factor 6; Arf6 | 7.0 |
| NM_126165 | Vacuolar protein sorting 4a (yeast); Vps4a | 6.9 |
| NM_009706 | Rho GTPase activating protein 5; Arhgap5 | 5.3 |
| AK080204 | Phosphatidylinositol binding clathrin assembly protein; Picalm | 5.3 |

TABLE 2-continued

Notably changed genes of PAP $^{-/-}$ prostates at the age of two months

| Accession number | Gene title | Change |
|---|---|---|
| NM_009003 | RAB4A, member of RAS oncogene family; Rab4a | 4.6 |
| NM_016721 | IQ motif containing GTPase activating protein 1; Iqgap1 | 4.6 |
| NM_021518 | RAB2, member of RAS oncogene family; Rab2 | 4.3 |
| Z22819 | RAB24, member of RAS oncogene family; Rab24 | 4.3 |
| X80333 | RAB18, member of RAS oncogene family; Rab18 | 4.3 |
| NM_009166 | Sorbin and SH3 domain containing 1; Sorbs1 | 4.3 |
| NM_009790 | Calmodulin 1; Calm1 | 4.0 |
| AK031143 | RAB11a, member of RAS oncogene family; Rab11a | 4.0 |
| NM_025887 | RAB5a, member of RAS oncogene family; Rab5a | 3.7 |
| NM_009391 | RAN, member of RAS oncogene family; Ran | 3.5 |
| NM_011072 | Profilin 1; Pfn1 | 3.5 |
| NM_145491 | Ras homolog gene family, member Q; Rhoq | 3.2 |
| NM_008112 | Guanosine diphosphate (GDP) dissociation inhibitor 3; Gdi3 | 3.2 |
| NM_007479 | ADP-ribosylation factor 4; Arf4 | 2.9 |
| NM_016802 | Ras homolog gene family, member A; Rhoa | 2.8 |
| NM_007483 | Ras homolog gene family, member B; Rhob | 2.6 |
| NM_010312 | Guanine nucleotide binding protein, beta 2; Gnb2 | 2.6 |
| NM_007478 | ADP-ribosylation factor 3; Arf3 | 2.5 |
| XM_127051 | Son of sevenless homolog 2; Sos2 | 2.5 |
| NM_026697 | RAB14, member of RAS oncogene family; Rab14 | 2.5 |
| | Downregulated in cell adhesion, actin cytoskeleton and microtubules | |
| NM_009258 | Serine protease inhibitor, Kazal type 3; Spink3 | 119 |
| NM_011847 | DnaJ (Hsp40) homolog, subfamily B, member 6; Dnajb6 | 45 |
| NM_010863 | Myosin 1b; Myo1b | 44 |
| NM_024427 | Tropomyosin I, alpha; Tpm1 | 42 |
| NM_007962 | Epithelial V-like antigen; Eva1 | 37 |
| NM_016705 | Kinesin family member 21A; Kif21a | 37 |
| NM_133669 | Retinis pigmentosa 2 homolog; Rp2h | 30 |
| NM_010135 | Enabled homolog (*Drosophila*); Enah | 28 |
| NM_023646 | DnaJ (Hsp40) homolog, subfamily A, member 3; Dnaja3 | 9.8 |
| NM_018748 | Golgi autoantigen, golgin subfamily a, 4; Golga4 | 8.0 |
| NM_009041 | Radixin; Rdx | 6.0 |
| NM_007616 | Caveolin 1; Cav1 | 4.9 |
| NM_007982 | PTK2 protein tyrosine kinase 2; Ptk2 | 4.3 |
| NM_009861 | Cell division cycle 42 homolog; Cdc42 | 4.0 |
| NM_024457 | RAS related protein 1b; Rap1b | 4.0 |
| NM_009007 | RAS-related C3 botulinum substrate 1; Rac1 | 3.0 |
| NM_009071 | Rho-associated coiled-coil forming kinase 1; Rock1 | 2.6 |
| | Downregulated in $Ca^{2+}$-signaling | |
| NM_175025 | ATPase, $Ca^{++}$-sequestering; Atp2c1 | 32 |
| NM_133926 | Calcium/calmodulin-dependent protein kinase I; Camk1 | 12 |
| NM_011313 | S100 Calcium binding protein A6 (calcyclin); S100a6 | 5.3 |

MAPK/Erk Signaling Pathway is Imbalanced and Akt is Functional

Several genes related to signaling through the mitogen-activated protein kinase/extracellular signal regulated kinase (MAPK/Erk) pathway were downregulated, including both activators and inactivators. Among the most down-regulated genes was Spred1 (−28×), which encodes a repressor of this survival pathway. Spred1 inhibits Raf kinase activation by interacting with Ras, which in turn is activated by a complex of Sos2 and Grb2. Spred1 localizes in a lipid raft/caveolae and inhibits MAPK/Erk activation in collaboration with caveolin1. The gene encoding caveolin1, Cav1, was downregulated −4.9×. Spred translocates to plasma membrane and binds to PI(4,5)P$_2$, which is essential for the downregulation of MAPK/Erk signaling. In addition, Sos2, a guanine nucleotide exchange factor and a positive regulator of Ras, was downregulated −2.5×. The genes for Dusp4, dual-specificity protein phosphatase 4, and Stk24, serine/threonine protein kinase 24, catalyzing the opposite reactions on Erk1 were both substantially and similarly downregulated (both −45×).

Western blot results showed an increased amount of PTEN phosphorylated at Ser380/Thr382/383, which is needed for its stability and activity (FIG. 6B). Protein kinase PDK1, which phosphorylates PKB/Akt, enhancing its activity, has 3.2× increased gene expression. The PKB/Akt signaling cascade was active, as evidenced by the phosphorylation of Akt and GSK3β, a direct downstream substrate of Akt. The gene expression of Akt and GSK3β was not changed. The pGSK3β antibody detected the Ser9-phosphorylated form that has an inhibitory effect.

It was found out that PAP dephosphorylates PI(3)P effectively and is on the endosomal pathway, and that knockout of PAP activity caused extensively decreased expression of Inpp5f, which is a known mechanism for increasing PI(4,5)P$_2$ concentration at the plasma membrane. It is a precursor of PI(3,4,5)P$_3$, which is, upon stimulation of tyrosine kinase and some GPCRs, increased by factors ranging from 2- to 100-fold. PI(3,4,5)P$_3$ accounts for a number of cellular functions via PI3K/Akt signaling: cell growth, proliferation, resistance to apoptosis, regulation of cytoskeleton dynamics, membrane trafficking, and responses of insulin, and it is a substrate of PTEN. Resting mammalian cells contain significant levels of PI(3)P, and it is under debate whether the overall level of PI(3)P is increased upon cellular stimulation. The levels of the other 3-PIs rise, but probably never reach the levels of PI(4,5)P$_2$ or PI(4)P. PI(3)P is associated with the endosome system and is at the lipid rafts subdomain of the plasma membrane after insulin induction. Both in yeast and in *C.*

*elegans*, ineffective PI 3-phosphatase (myotubularin)-mediated PI(3)P regulation resulted in redistribution of this lipid, enrichment on the vacuolar membrane and disturbed Arf6GTPase mediated endocytosis. Arf6 controls the PI(4,5)$P_2$ level both at the plasma membrane and in endosomes. Arf6 also regulates actin organization. PI(4,5)$P_2$ accumulation on endosomes leads to the formation of large vacuolar membrane structures preventing the membrane from recycling back to the plasma membrane. It has been concluded that the efficiency of the sorting of molecules into exosomes increases when the recycling kinetics of molecules decreases. In PAP$^{-/-}$ prostates, exocytosis was increased. PAP has a putative cholesterol binding domain, but its effect on cholesterol-dependent clusters is not known. One mechanism underlying the detected reduced secretion of PAP$^{-/-}$ epithelial cells of prostate may be cholesterol depletion. Inactivation of PI-phosphatases results in disturbed vesicular/membrane trafficking. Synaptojanin 1, which is a presynaptic PI-phosphatase, is a regulator of synaptic vesicle recycling, and neurons of synanpojanin 1-deficient mice show elevated PI(4,5)$P_2$ levels and accumulation of clathrin-coated vesicles in nerve endings.

The disorganization of myofibrils and the vesicular accumulations detected in PAP$^{-/-}$ mouse muscle cells are similar to the changes in myotubularin (MTM1) knockout mice. MTM1 specifically dephosphorylates PI(3)P. Charcot-Marie-Tooth disease (CMT) types I and 4A and B are demyelinating neuropathies caused by defects in various genes. Mutation in myotubularinrelated protein 2 (MTMR2), also a PI 3-phosphatase, causes neuropathic CMT 4B1. This demyelinating motor and sensory neuropathy is characterized by the presence of focally folded myelin sheaths. CMT 2B, which is a peripheral sensory axonal neuropathy causing sensory loss and distal muscle weakness and atrophy, is linked to chromosome 3q21, and thereby to the missense mutation in Rab7 colocalizing with PI(3)P to late endosomes. The chromosomal location of PAP was mapped to 3q21-q23.

Unusually numerous G-protein/small G-protein signaling genes were downregulated. Similarly to Arf6, another endosomal regulator, Rab5, was downregulated in PAP$^{-/-}$ prostates. It regulates the production of PI(3)P by directly phosphorylating PI via PI3K or by interacting with an enzymatic cascade of PI3K, PI5 and PI4-phosphatases. It can directly interact with a microtubule motor and stimulate the stable association of endosomes with microtubules by regulating endosomal docking, fusion, and motility on microtubules. Downregulation of Rab5a has been observed in metastatic prostate cancer and is suggested to have a role in oncogenesis. An interesting question is how PAP is transported onto the endosomal pathway. It is secreted both in prostate and in salivary gland. In saliva, it may also have phytase activity. It has a lysosomal targeting signal and is detected in lysosomes. It also has putative caveolin and cholesterol-binding domains, and we conclude that it might be taken back into cells by the endosomal pathway, but the exact mechanism is under investigation. A remarkable amount of G-protein/small G-protein signaling genes were changed, suggesting that PAP is functional on plasma membrane and endosomal pathway.

In conclusion, the study provides evidence that PAP is a novel PI3-phosphatase and an important regulator of the amount/equilibrium and local distribution of phosphatidylinositol phosphates. This finding constitutes the molecular basis for the disease mechanism in prostate adenocarcinoma, myopathy, and neuropathy involving disturbed G-protein signaling together with disordered vesicular/membrane trafficking and cytoskeletal organization.

EXPERIMENTAL SECTION

Generation of PAP Deficient Mouse

In order to analyze the physiological function and significance of PAP, mice with a modified PAP gene were generated. Neomycin phosphotransferase (neo) gene was inserted into exon 3 of the PAP genomic fragment (FIG. 1A) and gene targeting was carried out in embryonal stem (ES) cells. Homologous recombination at the PAP locus occurred in two out of 27 ES cell clones analyzed by PCR. Homozygous PAP$^{\Delta 3/\Delta 3}$ mice with homogenous genetic background were generated using standard methods and correct targeting was confirmed with Southern blot analyses (FIG. 1B). PAP present in PAP$^{-/-}$ mice was catalytically inactive.

Generation of PAP$^{\Delta 3/\Delta 3}$ Deficient Mouse

129SVJ/Lambda FIXII mouse genomic DNA library (Stratagene) was screened with the cDNA encoding rPAP (Roiko et al.: Primary structure of rat secretory acid phosphatase and comparison to other acid phosphatases, Gene 1990, 89(2): 223-9; Porvari et al., Differential androgen regulation of rat prostatic acid phosphatase transcripts, Biochem Biophys Res Commun 1995, 213(3):861-8). Genomic clone of the mPAP containing exons 3-7 was isolated. An around 7 kb BamHI fragment of this clone was used as a base of the targeting construct. Neo gene from pTV-O vector was cloned into the exon 3 near the 5' end of the construct. Thymidine kinase (tk) gene was added after the long arm of mPAP sequence. The linearized targeting construct was electroporated into ES cells, and clones were selected according to G-418 and ganciclovir resistance. Correct targeting was screened by PCR and positive clones were further analyzed with Southern blotting. The microinjection method was used to generate chimeric mice and back-crossing was carried out in order to obtain PAP$^{-/-}$ mice with a homogeneous genomic background.

The removal of acid phosphatase activity of PAP$^{-/-}$ in prostate lobes was confirmed with activity staining of native PAGE of tissue homogenates (Vihko et al., 1993, Proc. Natl. Acad. Sci. U.S.A. 90, 799-803).

Domain Analyses of PAP

Domain analyses were performed using the SMART (http://smart.emblheidelberg.de) and InterProScan (http://www.ebi.ac.uk/InterProScan) programs.

Analyses of PAP Substrates

Modeling of the binding of phosphoinosides with the phosphate group in different positions was performed. The protein side chains were kept fixed.

The binding of human PAP to phospholipids was screened using PIP Strips™ (Echelon Bioscience). 100 pmole of lysophosphatidic acid, lysophosphocholine, PI, PI(3)P, PI(4)P, PI(5)P, phosphatidyletanolamine, phosphatidylcholine, sphingosine-1-phosphate, PI(3,4)$P_2$, PI(3,5)$P_2$, PI(4,5)$P_2$, PI(3,4,5)$P_3$, phosphatidic acid, and phosphatidylserine was immobilized on a nitrocellulose strip. The strip was incubated with 10 µg/ml or 50 µg/ml human PAP in 4% non-fat dry milk (Valio) in TBS-T overnight at +4° C. The bound PAP was detected using polyclonal PAP antibody produced by us (Vihko et al., 1978, Clin. Chem. 24, 1915-1919), alkalinephosphatase conjugated secondary antibody (Sigma), and the NBT/BCIP color reaction assay (Promega).

A malachite green assay (BIOMOL GREEN™, BIOMOL Research Laboratories, Inc.) adapted to a 96-well format was used to measure the released free-phosphate from PI(3)P (Echelon Bioscience Inc.). Briefly, the reaction (total volume of 25 μl) containing 50 mM MES buffer, pH 6.5 and an indicated amount of PI(3)P, was initiated by adding the PAP (0.25 μg per reaction) purified from human spermatic fluid as previously described (specific activity of the enzyme 397 μmol min$^{-1}$ mg$^{-1}$) (Vihko et al. 1978, Clin. Chem. 24, 1915-1919). After incubation at 37° C. for 2 and 5 min the reaction was terminated by adding 100 μl of BIOMOL GREEN reagent. The green color was allowed to develop for 20 min at room temperature and absorbance was measured at 650 nm. The phosphate released was quantified by comparing to inorganic phosphate standards. Each data point was assayed in duplicate, and the experiment was repeated three times.

Histopathology

Mouse prostates were formalin-fixed and embedded in paraffin. Five-micron sections were cut and stained with hematoxylin and eosin for light microscopy analyses performed independently by pathologists. Evaluation of histopathology was done according to Park et al., 2002 Am. J. Pathol. 161, 727-735; Roy-Burman et al., 2004 Endocr. Relat. Cancer 11, 225-254; and Sakr et al., 2004, Prostatic Intraepithelial Neoplasia. In Pathology and Genetics of Tumours of the Urinary System and Male Genital Organs, J. N. Eble, G. Sauter, J. I. Epstein, and I. A. Sesterhenn, eds. (Lyon, France, IARCPress), 193-198.

RNA Isolation and Microarray Analysis

Total RNA was purified from different prostate lobes of mice aged 1, 2 and 6 months with RNA RNeasy Midi kit (Qiagen) and used for microarray analyses. Experimental procedures for GeneChip were performed according to the Affymetrix GeneChip Expression Analysis Technical Manual. In essence, using 8 μg of total RNA as template, double-stranded DNA was synthesized by means of the One-cycle cDNA synthesis kit (Affymetrix) and T7-(dT)24 primer. The DNA was purified using GeneChip Sample Cleanup Module (Qiagen). In vitro transcription was performed to produce biotin-labeled cRNA using IVT labeling kit (Affymetrix) according to the manufacturer's instructions. Biotinylated cRNA was cleaned with GeneChip Sample Cleanup Module (Qiagen), fragmented to 35 to 200 nt, and hybridized to Affymetrix MOE430A or MOE430_2.0 arrays that contain approximately 20,000 and 40,000 mouse transcripts, respectively. After being washed, the array was stained with streptavidin-phycoerythrin (Molecular Probes). The staining signal was amplified by biotinylated anti-streptavidin (Vector Laboratories) and second staining with streptavidin-phycoerythrin, and then scanned on GeneChip Scanner 3000.

The expression data were analyzed using Affymetrix GeneChip Operating System software. Signal intensities of all probe sets were scaled to the target value of 500. The results were analyzed using the Onto-express tools program (Intelligent Systems and Bioinformatics Laboratory).

Proliferation and Apoptosis Analyses

Cell proliferation indexes of AP and DLP of PAP$^{-/-}$ and PAP$^{+/+}$ mice were determined by Ki67 staining (NovoCastra) with Histomouse™-max kit (Zymed® Laboratories Inc.) and counterstained with hematoxylin. Three μm paraffin sections were cut onto silane (Sigma) treated slides for proliferation analyses.

The number of apoptotic cells in PAP$^{-/-}$ and PAP$^{+/+}$ specimens was determined from 5 μm paraffin sections of AP and DLP by Tunnel assay using ApopTag Peroxidase in situ Apoptosis Detection Kit (Chemicon International). Five fields of the gland were photographed, each field was divided into 16 segments and the cells were counted separately. Statistical analyses were performed by Student's two-tailed t-test.

Immunoblotting

Tissue lysates were prepared from four-to-five-months-old PAP$^{+/+}$ and PAP$^{-/-}$ DLP lobes using 1 mM sodium orthovanadate containing lysis buffer to prevent endogenous phosphatase activity. Total amount of 40 μg of protein was loaded into the wells and proteins were separated by SDS-PAGE and analyzed by Western immunoblotting. Antibodies against pPTEN and pGSK3β were purchased from Cell Signaling Technology and used according to the manufacturer's recommendation.

Transmission Electron and Immunoelectron Microscopies

Tissue specimens from mouse prostate lobes were fixed in 1% glutaraldehyde, 4% formaldehyde mixture in 0.1 M phosphate buffer for transmission electron microscopy (TEM). They were postfixed in 1% osmiumtetroxide, dehydrated in acetone and embedded in Epon Embed 812 (Electron Microscopy Sciences). Thin sections were cut with a Reichert Ultracut ultramicrotome and examined in a Philips CM100 transmission electron microscope. Images were captured by CCD camera equipped with TCL-EM-Menu version 3 from Tietz Video and Image Processing Systems GmbH.

Fresh prostate tissues were fixed in 4% paraformaldehyde in 0.1 M phosphate buffer, pH 7.4 for 2 hours, immersed in 2.3 M sucrose and frozen in liquid nitrogen for immunoelectron microscopy (IEM). Thin cryosections were cut with Leica Ultracut UCT microtome. For the single and double immunolabeling, the sections were first incubated in 5% BSA, 0.1% gelatin in PBS. Antibodies and gold conjugates were diluted in 0.1% BSA-C (Aurion) in PBS. All washings were performed in 0.1% BSA-C in PBS.

For the single labeling experiment, the sections were incubated with antibodies to PAP followed by protein A-gold complex (size 10 nm) for 30 min, made after Slot and Geuze, 1985, Eur. J. Cell Biol. 38, 87-93.

It will be appreciated that the methods of the present invention can be incorporated in the form of a variety of embodiments, only a few of which are disclosed herein. It will be apparent for the expert skilled in the field that other embodiments exist and do not depart from the scope of the invention. Thus, the described embodiments are illustrative and should not be construed as restrictive.

The invention claimed is:

1. A method of screening for a compound that decreases PI(4,5)P$_2$ accumulation or decreases PI(3)P levels comprising:
   (a) administering said compound to a knockout mouse whose genome comprises a homozygous disruption in a nucleic acid encoding prostatic acid phosphatase (PAP), wherein said disruption results in the null inactivation of PAP and wherein said knockout mouse exhibits prostatic atypical hyperplasia, prostatic intraepithelial neoplasia, adenocarcinoma of the prostate, myopathy or neuropathy; and
   (b) determining if said administered compound decreases PI(4,5)P$_2$ accumulation or decreases PI(3)P levels compared to PI(4,5)P$_2$ accumulation or PI(3)P levels in a knockout mouse whose genome comprises a homozygous disruption in a nucleic acid encoding PAP, wherein said disruption results in the null inactivation of PAP not administered said compound;
   wherein said decreased PI(4,5)P$_2$ accumulation or said decreased PI(3)P level indicates that said compound is a candidate therapeutic for treating disorders related to increased PI(4,5)P$_2$ accumulation or increased PI(3)P levels.

2. The method of claim 1, comprising screening for a compound that decreases PI(4,5)P$_2$ accumulation.

3. The method of claim 1, comprising screening for a compound that decreases the level of PI(3)P.

4. The method of claim 1, wherein said disruption has been introduced exon 3 of the PAP gene.

5. The method of claim 1, wherein said disorder is prostatic atypical hyperplasia, prostatic intraepithelial neoplasia or adenocarcinoma of the prostate.

6. The method of claim 1, wherein said disorder is myopathy or neuropathy.

* * * * *

SEQUENCE LISTING

<160> NUMBER OF SEQ ID NOS: 11

<210> SEQ ID NO 1
<211> LENGTH: 20
<212> TYPE: DNA

<213> ORGANISM: Artificial Sequence
<220> FEATURE:
<223> OTHER INFORMATION: Synthetic primer

<400> SEQUENCE: 1
tgctgcacgg atacacatgc                                               20

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
tcgcagcgca tcgccttct                                                19

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Lys Ser Arg Leu Gln
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Lys Arg Ala Thr Gln
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Phe Leu Phe Leu Leu Phe Phe Trp
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Tyr Arg Lys Phe Leu Asn Glu Ser Tyr
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide -continued

```
<400> SEQUENCE: 7

Leu Gly Glu Tyr Ile Arg Lys Arg Tyr Arg
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Leu Leu Tyr Leu Pro Phe Arg
1               5

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide

<400> SEQUENCE: 9

Leu Ser Leu Leu Ser Leu Tyr Gly Ile His Lys Gly Lys
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Leu Thr Glu Leu Tyr Phe Glu Lys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Val Glu Met Tyr Val Arg
1               5
```